(12) United States Patent
Frohwitter

(10) Patent No.: US 11,684,805 B2
(45) Date of Patent: Jun. 27, 2023

(54) DEVICE FOR THE ULTRASOUND TREATMENT OF OPEN WOUNDS

(71) Applicant: Jens-Christian Frohwitter, Neusäß (DE)

(72) Inventor: Jens-Christian Frohwitter, Neusäß (DE)

(73) Assignee: Jens-Christian Frohwitter, Neusäß (DE)

( * ) Notice: Subject to any disclaimer, the term of this patent is extended or adjusted under 35 U.S.C. 154(b) by 608 days.

(21) Appl. No.: 15/121,952

(22) PCT Filed: Jan. 22, 2016

(86) PCT No.: PCT/EP2016/051379
§ 371 (c)(1),
(2) Date: Aug. 26, 2016

(87) PCT Pub. No.: WO2016/116623
PCT Pub. Date: Jul. 28, 2016

(65) Prior Publication Data
US 2017/0072224 A1    Mar. 16, 2017

(30) Foreign Application Priority Data
Jan. 22, 2015   (DE) .................... 10 2015 201 092.9

(51) Int. Cl.
*A61N 7/00* (2006.01)
*A61N 5/06* (2006.01)
(Continued)

(52) U.S. Cl.
CPC .............. *A61N 7/00* (2013.01); *A46B 13/023* (2013.01); *A46B 15/0028* (2013.01);
(Continued)

(58) Field of Classification Search
CPC ... A61B 90/98; A46B 13/023; A46B 15/0028; A46B 2200/1006; A61N 7/00;
(Continued)

(56) References Cited

U.S. PATENT DOCUMENTS 5,697,230 A * 12/1997 Ender ................. A47L 15/4445
68/3 SS
6,478,754 B1 * 11/2002 Babaev ............... A61M 11/005
601/2

(Continued)

FOREIGN PATENT DOCUMENTS

AU      2012202212 B2   4/2014
DE    102006027789 A1  12/2006
(Continued)

OTHER PUBLICATIONS

International Search Report for International Application No. PCT/EP2016/051379, dated May 3, 2016.

*Primary Examiner* — Keith M Raymond
*Assistant Examiner* — Sean A Frith
(74) *Attorney, Agent, or Firm* — Marshall, Gerstein & Borun LLP

(57) ABSTRACT

An ultrasound-assisted wound cleanser in the form of a handheld device includes an integrated vibration motor, an integrated ultrasound generator, an integrated energy source for the vibration motor and the ultrasound generator, and a replaceable cleansing attachment which can be driven by the vibration motor for abrasively removing wound coatings. The cleansing attachment has an acoustic transducer which is designed to convert the electric oscillations generated by the ultrasound generator into sound waves, a device for reinforcing and/or distributing and/or transferring the ultrasound waves, and bristles and/or lamellas for the abrasive removal. Further, a method for cleansing wounds includes moving a cleansing attachment with bristles for abrasively (Continued)

removing wound coatings by a vibration motor. The cleansing attachment is oscillated by an ultrasound generator, and the oscillations for supporting the removal of wound coatings are transmitted into the wound via a transmission medium.

14 Claims, 2 Drawing Sheets

(51) Int. Cl.
  *A61B 90/98* (2016.01)
  *A46B 13/02* (2006.01)
  *A46B 15/00* (2006.01)

(52) U.S. Cl.
  CPC ............ *A61B 90/98* (2016.02); *A61N 5/0624* (2013.01); *A46B 2200/1006* (2013.01); *A61N 2005/0644* (2013.01); *A61N 2005/0661* (2013.01); *A61N 2007/0017* (2013.01)

(58) Field of Classification Search
  CPC .......... A61N 5/0624; A61N 2005/0644; A61N 2005/0661; A61N 2007/0017
  See application file for complete search history.

(56) References Cited

U.S. PATENT DOCUMENTS

| | | | |
|---|---|---|---|
| 6,569,170 B1 | 5/2003 | Kellogg | |
| 8,533,893 B2* | 9/2013 | Sayeed | A46D 1/0215 15/167.1 |
| 8,978,278 B1* | 3/2015 | Rossi | A46B 15/00 40/314 |
| 2004/0030254 A1 | 2/2004 | Babaev | |
| 2004/0143918 A1* | 7/2004 | Blackman | A46B 7/04 15/28 |
| 2005/0033201 A1 | 2/2005 | Takahashi et al. | |
| 2005/0278877 A1 | 12/2005 | Akridge et al. | |
| 2007/0011836 A1 | 1/2007 | Brewer et al. | |
| 2007/0219470 A1 | 9/2007 | Talish et al. | |
| 2008/0058648 A1* | 3/2008 | Novak | A61B 17/22004 600/471 |
| 2008/0209650 A1* | 9/2008 | Brewer | A46B 15/0002 15/22.1 |
| 2008/0286145 A1 | 11/2008 | Ratcliffe | |
| 2009/0042870 A1* | 2/2009 | Fellows | A01N 39/00 514/224.8 |
| 2009/0177125 A1 | 7/2009 | Pilcher et al. | |
| 2010/0221205 A1* | 9/2010 | Blin | A61K 8/19 424/63 |
| 2011/0121049 A1* | 5/2011 | Malinouskas | A61B 90/98 227/175.1 |
| 2011/0125138 A1* | 5/2011 | Malinouskas | A61B 17/068 606/1 |
| 2011/0284024 A1 | 11/2011 | Trebella et al. | |
| 2012/0204898 A1* | 8/2012 | Haley | A46B 11/0037 132/309 |
| 2013/0209158 A1* | 8/2013 | Ziadeh | A46B 11/0062 401/143 |
| 2013/0308994 A1* | 11/2013 | Wu | A46D 3/00 401/188 R |
| 2014/0031726 A1 | 1/2014 | Chernomorsky et al. | |
| 2014/0135798 A1* | 5/2014 | David | A61B 17/54 606/131 |
| 2014/0200481 A1* | 7/2014 | Johnson | A61M 5/14236 600/561 |
| 2014/0336540 A1* | 11/2014 | Chen | A61N 7/00 601/2 |
| 2015/0033488 A1* | 2/2015 | Varila | A46B 9/026 15/167.1 |
| 2015/0047134 A1* | 2/2015 | Prendergast | A46B 13/023 15/4 |
| 2015/0216525 A1* | 8/2015 | Collins | H05K 7/06 227/176.1 |
| 2016/0143718 A1* | 5/2016 | Serval | A46B 15/0006 15/22.1 |

FOREIGN PATENT DOCUMENTS

| | | |
|---|---|---|
| JP | H11318917 A | 11/1999 |
| JP | 2002085300 A | 3/2002 |
| RU | 2271182 C1 | 3/2006 |
| WO | WO-2004/014284 A1 | 2/2004 |
| WO | WO-2006/119376 A2 | 11/2006 |

\* cited by examiner

DEVICE FOR THE ULTRASOUND TREATMENT OF OPEN WOUNDS

CROSS-REFERENCE TO RELATED APPLICATIONS

This is the United States national phase of International Patent Application No. PCT/EP/2016/051379, filed Jan. 22, 2016, which claims the priority benefit of German Application No. 10 2015 201 092.9, filed Jan. 22, 2015. Each of the foregoing is expressly incorporated herein by reference in the entirety.

FIELD OF THE DISCLOSURE

The invention relates to an ultrasound-assisted wound cleanser in the form of a handheld appliance, and to a method for cleansing wounds.

BACKGROUND

Various ways and devices for cleansing wounds are known from the prior art. For example, US 2005/0278877 A1 discloses a brush for cleansing chronic wounds. The brush has a rotary drive for moving the brush in rotation.

Ultrasound-assisted wound cleansers are also known from the prior art. Known systems of the kind produced, for example, by Soring GmbH or by Misonix Inc. have a stationary unit and a handheld part that is connected via hoses. The stationary unit accommodates a pump, for delivery of an irrigation liquid and coupling liquid, and also an ultrasound generator. The handheld part connected thereto via hoses comprises a cleansing attachment, which is made of metal and is set in ultrasonic oscillation, and an opening through which the liquid delivered from the stationary base is able to enter the wound.

Moreover, methods of water-jet wound debridement or of surgical wound cleansing are also known that are very invasive and that are therefore used only in exceptional cases, particularly when tissue is to be removed from a large area.

The methods of mechanical wound cleansing, in particular by brushes or swabs, are an inexpensive and frequently used way of cleansing wounds. However, they have the disadvantage that the destruction and removal of the biofilm located in the wound is only very limited, which leads to the treatment being frequently repeated. Cleansing of wounds by ultrasound affords better results here, particularly as regards the removal of the biofilm. However, disadvantages of the known systems are the high investment costs for the equipment, the limited mobility, and the elaborate preparation and reconditioning of the treatment location necessitated by the spread of germs caused by the aerosols that arise during use and by the liquid that is atomized for ultrasound transmission and for irrigating the wound.

GENERAL DESCRIPTION

The object of the present invention is to make available a device, a method and a system for effective wound cleansing, all of which are cost-effective, require no preparatory work and reconditioning and can be used at any desired location where the patient is present.

The ultrasound-assisted wound cleanser according to the invention in the form of a handheld appliance has an integrated vibration motor, an integrated ultrasound generator, an integrated energy source for the vibration motor and for the ultrasound generator, and a replaceable cleansing attachment which can be driven by the vibration motor for the purpose of abrasively removing wound coatings. The cleansing attachment has an acoustic transducer, preferably a piezo crystal, which is connected to the ultrasound generator, and a device for strengthening and/or distributing and/or transmitting the ultrasound waves. The acoustic transducer converts the high-frequency current generated by the generator into ultrasonic oscillations depending on its amplitude and its frequency.

In this context, the handheld appliance is regarded in particular as a portable, handheld and/or mobile ultrasonic cleansing appliance. Such a handheld appliance operates in particular without a power supply unit which is not handheld and which during the treatment is connected to the handheld appliance. Such power supply units have in particular assemblies such as pumps and/or sound generators. Thus, during use, i.e. during the wound cleansing, the handheld instrument is autonomous and easy to handle. The design as a mobile handheld appliance affords the possibility of the patients being treated, for example, at home by their general practitioner or by healthcare visitors.

The handheld appliance comprises a base, in which the vibration motor, the ultrasound generator and the energy source are integrated. A replaceable cleansing attachment for the abrasive removal of wound coatings can be connected to the base. The cleansing attachment preferably has bristles and/or lamellas for the mechanically abrasive removal of wound coatings. The front area of the cleansing attachment, which is formed by the bristles and/or lamellas, will also be referred to as the bristle head or cleansing head. During cleansing of the wound, the bristle head protrudes past the other structural parts of the cleansing attachment. The bristles and/or lamellas preferably have such a length that, during operation, they protrude farthest forward and form an exposed cleansing surface. It is thus ensured that different wound topographies, in particular plane or concave wound surfaces, can be reliably cleaned with the bristles and/or lamellas. Moreover, other structural parts of the cleansing attachment should not interfere with the abrasion of the wound coatings, in particular of the fibrin coatings, by the cleansing head or the bristles and/or lamellas, and preferably only the bristles and/or lamellas should be in engagement with the wound surface.

The bristles and/or lamellas are suitable in particular for the removal of fibrin coatings arising from blood coagulation and are preferably made of plastic or of synthetic fibers. More preferably, the cleansing attachment has one or more bristle rings which, for example, are arranged concentrically with respect to the acoustic transducer and/or to the device for strengthening and/or distributing and/or transmitting the ultrasound waves. In the configuration with more than one bristle ring, one of the bristle rings is arranged on the cleansing attachment, preferably encircling the device for strengthening and/or distributing and/or transmitting the ultrasound waves, in such a way that a propagation of aerosols is suppressed. The bristle ring thus forms a "protective shield" or a barrier against contamination, in particular against the propagation of aerosols contaminated with bacteria, which barrier prevents contamination of adjacent skin areas and of the environment. For the cleansing of deep, channel-shaped wounds, the bristle head is preferably designed in the manner of a pipe cleanser, in which the bristles protrude radially.

Moreover, the cleansing head preferably comprises a sonotrode. The sonotrode increases the amplitude of the ultrasound waves and serves as a transmitter of the sound waves. The shape of the sonotrode and the surface of the sonotrode vary depending on the area of use. For example, the shape of the sonotrode can cause a radial or axial emission of the ultrasound waves with respect to the longitudinal extent of the cleansing attachment. Depending on the design of the sound distributor and/or of the sonotrode, the ultrasound waves can be focussed or defocussed. The cleansing attachment is adaptable to different uses through the design of the sound distributor and/or of the sonotrode.

The vibration motor preferably operates with a frequency of 100 to 5000 Hz, more preferably with a frequency of 100 to 500 Hz, which is further preferably adjustable. The vibration motor is arranged in the base of the handheld appliance and is designed in such a way that the replaceable cleansing attachment and in particular the cleansing head and the bristles/lamellas can be driven by the vibration motor. The connection between base and cleansing attachment is preferably provided by a form-fit plug-in connection and has a drive mechanism, for example as is used in electric toothbrushes. The cleansing attachment is in particular designed in such a way that the bristles and/or lamellas can be driven by the vibration motor, in particular driven intermittently in rotation.

The ultrasound generator preferably generates a frequency of 20 kHz to 2 MHz, more preferably 20 kHz to 1 MHz, more preferably 20 kHz to 500 kHz, more preferably 20 kHz to 100 kHz, more preferably 20 kHz to 50 kHz. The frequency generated by the ultrasound generator and/or the amplitude is in particular adjustable. In a system according to the invention composed of ultrasound-assisted wound cleanser and transmission medium, the ultrasound waves introduced into the wound cause microcavitation in a transmission medium, for example an irrigation liquid or a gel, such that mechanical forces burst open the biofilm present in the wound. Thus, the bacterial coatings contained in the biofilm are removed. Moreover, the bursting open of the biofilm improves the efficacy of disinfectant solutions. The ultrasound signal additionally effects stimulation of the metabolism of the bacteria, such that the disinfectants are better absorbed by the bacteria and have a better action. The ability of the bacteria to adhere to one another is also limited. This in particular counteracts new formation of the biofilm.

The ultrasound-assisted wound cleanser preferably has a cleansing attachment identification device. The cleansing heads are in this case preferably linked to the hand-held apparatus by software coding. In this way, the type of the cleansing attachment used, its operating scope and the technical constraints, for example the bristle shape, can in particular be identified by the base. The cleansing attachment can thus be operated in an optimal manner. Moreover, repeated use of cleansing attachments can be avoided through the identification device. In particular, identification of the cleansing attachment, for example in a memory in the cleansing attachment, prevents reuse of the cleansing attachment. Identification as used generally takes place upon the first setting up of the wound cleanser with the respective cleansing attachment. The use of unsuitable cleansing attachments can also be prevented by an identification device of this kind. Preferably, the communication between base and cleansing attachment is coded. The communication between base and cleansing attachment can be by cable or alternatively by radio, for example using RFID technology.

More preferably, the cleansing attachment comprises a UV diode for irradiating the wound with UV light during the treatment. The irradiation with UV light provides an additional antimicrobial action, which supports the wound cleansing and also the wound healing.

The wound cleanser preferably comprises an inductive charger for charging the accumulator used as the energy source. In this way, the energy source of the wound cleanser can be charged in a simple manner. For this purpose, a base station is generally used which has a mains part. During the use of the wound cleanser, this external base station is not required and the wound cleanser is detached from the base station, such that it constitutes a compact and handheld wound cleanser. The wound cleanser in the form of a handheld appliance only has a weight of the order of approximately 100 g and can thus be easily carried to the patient who is to be treated.

The wound cleanser has in particular control electronics for controlling the various functions, such as ultrasound generation, vibration generation and, optionally, UV light treatment. The control electronics preferably comprise a press button or switch for switching on and off and for preselecting various operating modes, for example different frequencies, or for selecting individual functions. The activated functions and/or selected frequencies are in this case preferably indicated by LEDs or a display. The control electronics regulate the modules arranged in the base, for example the ultrasound generator or the vibration motor. The electrical oscillations of the ultrasound generator are transmitted via electrical leads to the acoustic transducer in the cleansing attachment. Moreover, the cleansing attachment identification and the UV diode optionally comprise electrical lines from the base into the cleansing attachment. These will transmit via electrical contacts on the base or on the cleansing attachment.

The cleansing attachment can moreover be designed with a disposable protective cover, which is stretched across the base of the wound cleanser. In this way, the base is protected against contamination during the treatment, and the cover is discarded together with the cleansing attachment after the treatment has ended.

In the method according to the invention for cleansing wounds, a cleansing attachment with bristles for abrasively removing wound coatings is moved via a vibration motor. The cleansing attachment is set in oscillation via an ultrasound generator, and the oscillations for assisting in the detachment of wound coatings are transmitted into the wound via a transmission medium 32.

As the transmission medium, in particular for the sound waves from the cleansing attachment into the wound, use is preferably made of a water-based medium or a gel. Before the start of the wound cleansing, the transmission medium is applied either to the wound to be cleaned and/or to the bristle head. The cleansing attachment can also have a gel reservoir, which continuously empties during the treatment. Wound coatings are removed abrasively by the movement of the bristles caused by the vibration motor. During the wound cleansing method, regular cleansing of the bristle head should take place. There is also the possibility of replacing contaminated transmission medium and/or of adding new transmission medium. The ultrasound waves are transmitted to the wound surface by the transmission medium, and cavitation occurs in the transmission medium. The wound surface, in particular the biofilm on the wound surface, is forced open and removed by the bursting of the cavitation bubbles.

In the treatment of chronic wounds, in particular open wounds, the patient may experience pain. For this reason, the transmission medium can contain analgesic or anesthetic active substances. Moreover, substances that detach the wound coating and/or substances with a disinfecting action can be admixed to the gel. As solvent and disinfectant, use is made in particular of polyhexamethylene biguanide, also known as polyhexanide or PHMB, silver solutions and/or silver gels. In addition or alternatively, the disinfecting action in the method according to the invention can be increased by UV light.

The cleansing attachment and in particular the bristles can be moved in rotation or linearly by the vibration motor. The rotation movement or linear movement is preferably intermittent. The vibration motor preferably generates a vibration of the bristles with a frequency of 100 to 5000 Hz. The ultrasound generator, in the method according to the invention, generates a frequency of 20 kHz to 2 MHz, preferably 20 kHz to 1 MHz, more preferably 20 kHz to 500 kHz, more preferably 20 kHz to 100 kHz, more preferably 20 kHz to 50 kHz. The frequencies of the vibration motor and/or of the ultrasound generator are preferably adjustable.

The method according to the invention is preferably carried out using an above-described ultrasound-assisted wound cleanser according to the invention in the form of a handheld appliance.

The portable ultrasound-assisted wound cleanser according to the invention and the method according to the invention for cleansing wounds permit effective wound cleansing by combination of the abrasive removal of fibrin coatings via the bristles/lamellas and by the bursting open of the biofilm by the microcavitation caused by the ultrasound. According to the invention, the oscillations both of the vibration motor and of the ultrasound generator/acoustic transducer are used for the cleansing, preferably parallel in time. The method for treating wounds is therefore a selective and tissue-preserving method that can be carried out often and almost without limitation. The wound cleansing and also the wound healing can in particular be assisted by antimicrobial UV radiation or by substances in the transmission medium or gel. By virtue of its design as an autonomous, handheld applicator, the wound cleanser is available for a large number of patients and can be used on them.

BRIEF DESCRIPTION OF THE DRAWINGS

Further features and advantages of the invention will become clear from the following illustrative embodiments described with reference to the figures, in which.

DETAILED DESCRIPTION

Figure 1:
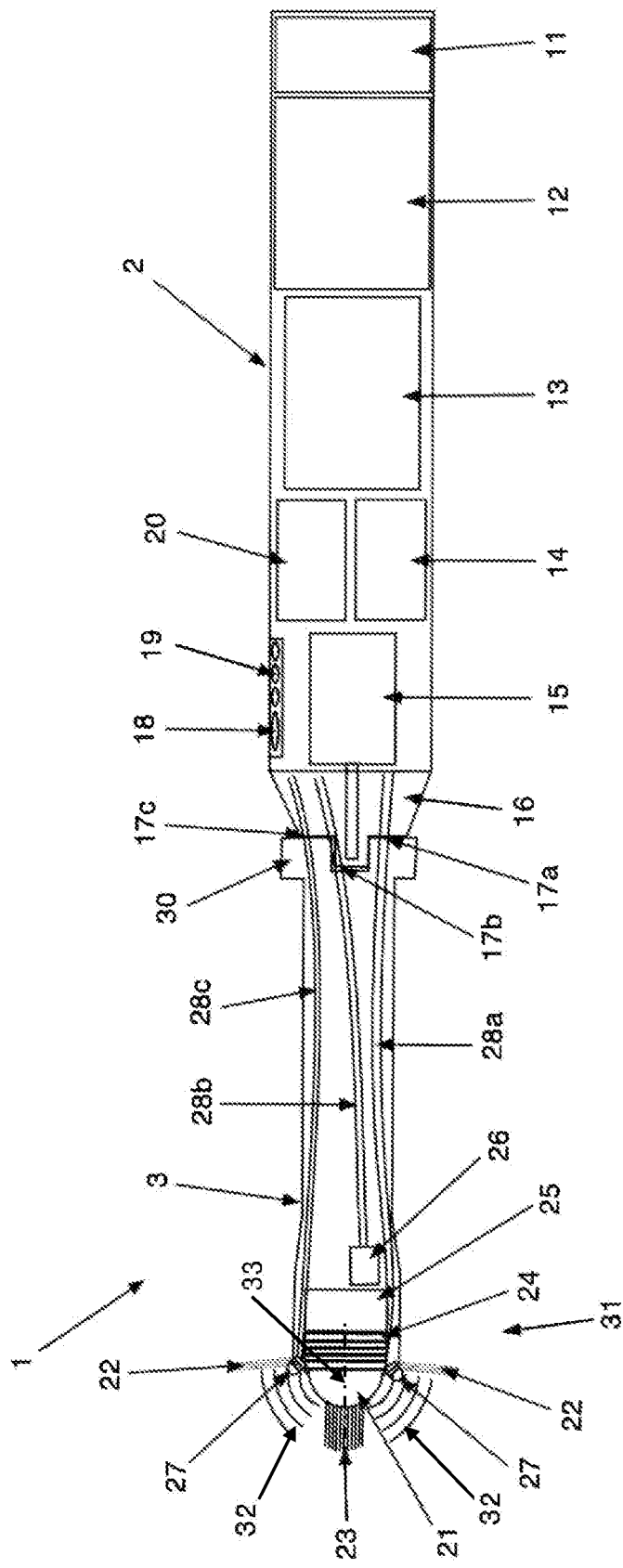
FIG. 1 shows an ultrasound-assisted wound cleanser in the form of a handheld appliance according to the invention.

FIG. 1 shows an ultrasound-assisted wound cleanser 1 according to the invention in the form of a handheld appliance. The wound cleanser comprises a base 2 and a replaceable cleansing attachment 3. The base 2 comprises an accumulator 12 and an inductive changer 11 for charging the accumulator 12. The base 2 moreover comprises an ultrasound generator 13, i.e. a generator for generating a high-frequency current. The frequency of the high-frequency current is adjustable between 20 kHz and 2 MHz via the control switch 18. The adjusted frequency is shown on the optical display element 19. The high-frequency current generated by the ultrasound generator 13 is conveyed via contact points 17a, 29a in the base 2 and in the cleansing attachment 3 and via an electrical lead 28a to an acoustic transducer 24. The acoustic transducer 24 is arranged in the front area of the cleansing attachment 3, the bristle head 31. The acoustic transducer 24 converts the high-frequency current into high-frequency ultrasound waves. A piezo crystal is used as acoustic transducer 24. The acoustic transducer 24 is connected to a counterweight 25, which is used as an inertial mass for generating the ultrasound waves and thus serves for the directed propagation of the sound waves. In addition, the sound waves are transmitted via a sonotrode 21 into the wound that is to be treated.

The base 2 further comprises a vibration motor 15. The output shaft of the vibration motor 15 is connected with form-fit engagement to the cleansing attachment 3 via a plug-in connector 30, in order to set bristles 22, 23 of the cleansing attachment into an intermittent rotary or linear movement via a mechanism not shown.

The wound cleanser 1 additionally has a system for identifying the attached cleansing attachment 3. For this purpose, a random access memory 14 is connected by contact points 17b, 29b and an electrical conductor 28b to a chip 26 in the cleansing attachment 3. Identification of the cleansing attachment ensures that the base 2 detects what kind of cleansing attachment 3 is involved and knows the technical data, for example nature of the bristles, functions of the cleansing attachment and the technical parameters of the latter. This makes it possible, on the one hand, that the cleansing attachment 3 is controlled according to its constraints. On the other hand, identification of the cleansing attachment ensures that each bristle attachment is used only once, so as to suppress transmission of germs. Moreover, identification of the cleansing attachment can eliminate the use of unapproved or incorrect cleansing attachments. To ensure also that an already used cleansing attachment cannot be used in connection with a second base 2, the use is stored on the chip 26 of the cleansing attachment 3.

The cleansing attachment 3 also has UV diodes 27 in its front area. The UV diodes emit UV radiation during the treatment, i.e. during operation of the wound cleanser 1, in order to kill germs. The UV diodes 27 are connected to the base 2 via the electrical conductor 28c and the contact points 29c and 17c and are accordingly controlled by said base 2.

To control the functions of the wound cleanser 1, such as ultrasound generation, vibration, UV irradiation and identification of the cleansing attachment, the base 2 has a control board 20. The latter is connected to the individual modules such as ultrasound generator 13 and vibration motor 15. In addition, the control board 20 is connected to the operating switch 18 and to a screen as visual display element 19, in order to adjust the various functions and modes or to display the current operating mode.

In its front area, the cleansing attachment 3 has a bristle ring 22, which encircles a longitudinal axis 33 of the acoustic transducer or the sonotrode 21 and suppresses the propagation of aerosols. The bristle ring 22 forms, as it were, a protective shield that avoids contamination of the environment. The bristles 23 arranged centrally on the cleansing head are provided for the mechanical or abrasive removal of wound coatings. When using the wound cleanser 1, in particular for cleansing chronic wounds, a cleansing attachment 3 packaged as a sterile disposable product is first of all placed onto the base 2. The cleansing attachment is identified by the cleansing attachment identification electronics, and the latter ascertain whether the cleansing attachment 3 is a suitable one. The operating parameters, for example the frequency and amplitude of the ultrasound generator, the frequency of the vibration motor and the use of the UV diode, are preselected via the operating switch 18.

The wound is pre-treated with a gel, i.e. a pain-relieving or numbing gel with disinfection substances is introduced into the wound. After a predefined duration of action, the wound is cleaned using the wound cleanser 1. On the one hand, fibrin coatings, i.e. products of blood coagulation, are removed from the wound by mechanical abrasion by means of the bristles 23. On the other hand, microcavitation is generated in the wound by the ultrasound, as a result of which the biofilm with its bacteria is forced open. After the cleansing attachment 3 has been put into operation, it is labeled in the chip 26 as having been used, such that further use of the same cleansing attachment 3 is prevented. This also serves to prevent inadvertent re-use on the next patient and therefore to prevent contamination. The cleansing attachment 3 is thus disposed of after it has been used once to clean a wound.

Figure 3:
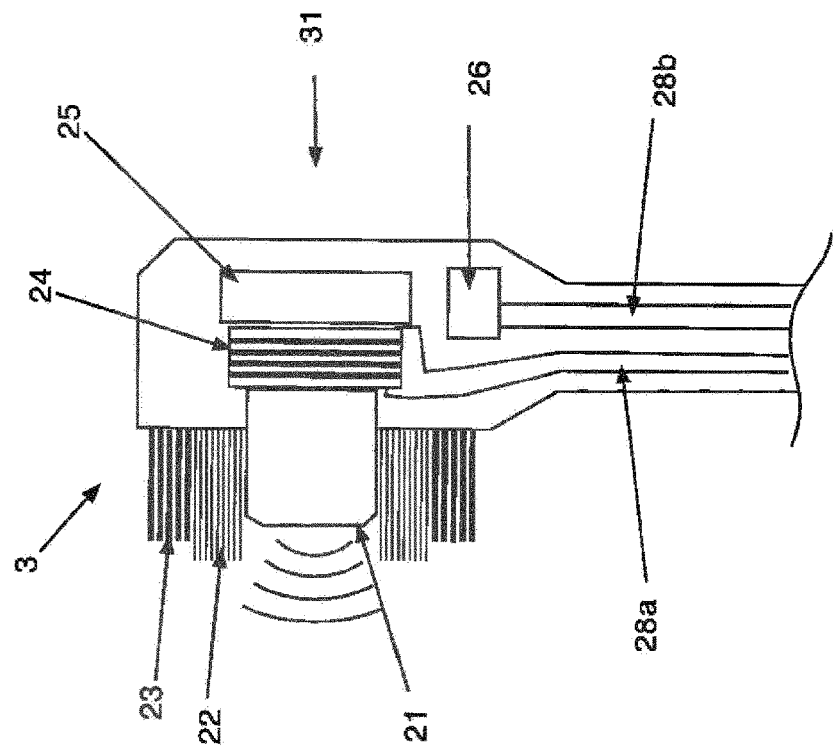
FIG. 3 shows a part of a further alternative cleansing attachment according to the invention.
Figure 2:
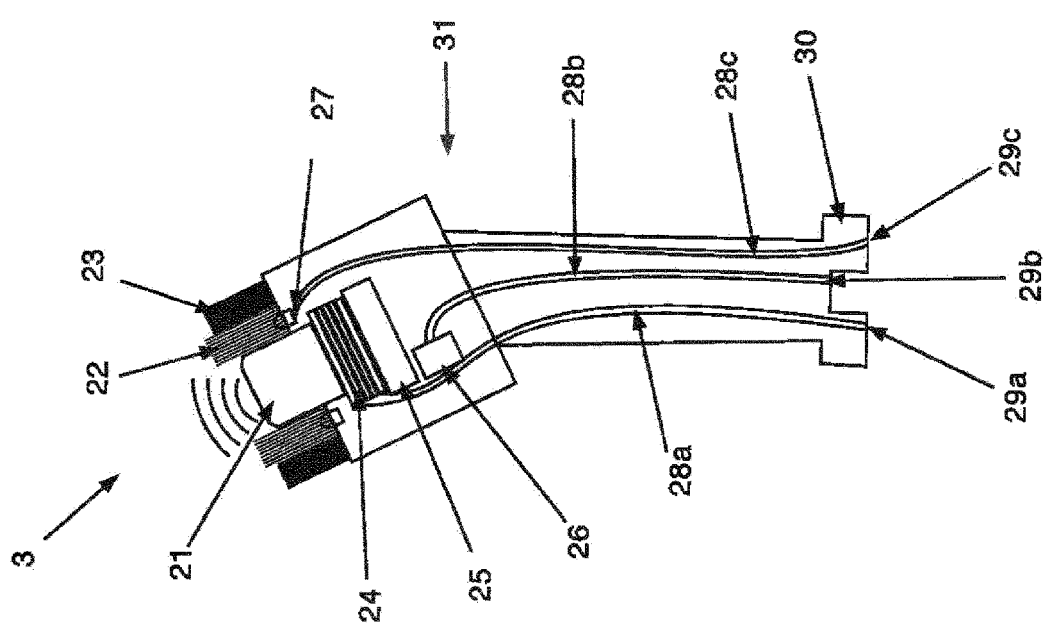
FIG. 2 shows an alternative cleansing attachment of a wound cleanser according to the invention.

FIGS. 2 and 3 show alternative embodiments of the cleansing attachment 3. The design of the cleansing attachments 3 differs depending on the type of wound that is to be cleaned. For deeper wound areas or wound pockets, the cleansing attachment 3 has a corresponding length and is optionally flexible, i.e. bendable to adapt to the shape of the wound. In contrast to the cleansing attachment 3 according to FIG. 1, the cleansing attachment shown in FIG. 2 has two bristle rings 22, 23. Both bristle rings 22, 23 are arranged concentrically around the sonotrode and protrude past the latter in the longitudinal direction of the bristles, such that an exposed cleansing surface is formed. The bristles 22, 23 and the bristle head 31 are inclined by a predefined angle with respect to the main orientation of the cleansing attachment 3.

The embodiment according to FIG. 3 differs from the embodiment according to FIG. 2 in that the cleansing attachment has no UV diodes for killing germs. In addition, the bristle head 31 is inclined by 90° to the main direction of extent of the cleansing attachment 3.

The invention claimed is:

1. An ultrasound-assisted wound cleanser in the form of a handheld appliance with a base and a replaceable cleansing attachment attached to the base, an integrated vibration motor, an integrated ultrasound generator, an integrated energy source for the vibration motor and for the ultrasound generator, and wherein the replaceable cleansing attachment can be driven by the vibration motor for the purpose of abrasive removal of fibrin wound coatings, wherein the replaceable cleansing attachment has an acoustic transducer, which is designed to convert the electric oscillations generated by the ultrasound generator into sound waves, and a device for transmitting the ultrasound waves, wherein the handheld appliance includes a cleansing attachment identification device adapted to ensure the replaceable cleansing attachment is used only once;
wherein the replaceable cleansing attachment has bristles arranged in an inner bristle rind encircling the device for transmitting the ultrasound waves to suppress a propagation of aerosols to the surrounding area and further bristles arranged in an outer bristle rind concentric to the inner bristle ring for the abrasive removal;
wherein the bristles of the inner bristle rind are longer than the bristles of the outer bristle ring,
wherein the cleansing attachment identification device comprises a chip in the replaceable cleansing attachment, and a control board and a memory in the base, wherein after a single use of the replaceable cleansing attachment, the chip is adapted to store a first use of the replaceable cleansing attachment thereon, and wherein the control board is configured to communicate with the chip, execute software code stored on the memory, and prevent a second use of the replaceable cleansing attachment when the chip has the first use of the replaceable cleansing attachment stored thereon.

2. The ultrasound-assisted wound cleanser as claimed in claim 1, characterized in that the bristles and are designed in such a way that they protrude past the other structural parts of the replaceable cleansing attachment during the wound cleansing.

3. The ultrasound-assisted wound cleanser as claimed in claim 1, characterized in that the vibration motor operates with an adjustable frequency of 100 to 5000 Hz.

4. The ultrasound-assisted wound cleanser as claimed in claim 1, characterized in that the ultrasound generator generates a frequency of 20 kHz to 2 MHz.

5. The ultrasound-assisted wound cleanser as claimed in claim 1, characterized in that the frequency generated by the ultrasound generator is adjustable.

6. The ultrasound-assisted wound cleanser as claimed in claim 1, characterized in that the energy source is an accumulator which can be charged via an inductive charger.

7. A method for cleansing a wound, in which method a replaceable cleansing attachment with bristles for the abrasive removal of wound coatings is moved via a vibration motor and arranged in such a way that a propagation of aerosols is suppressed, the replaceable cleansing attachment is oscillated via an ultrasound generator, and the oscillations are transmitted into the wound via a transmission medium containing a disinfectant for:
 (a) assisting in the detachment of fibrin wound coatings,
 (b) forcing, by microcavitation, biofilm in the wound to open, and
 (c) stimulating metabolism of bacteria in the wound for the bacteria to better absorb disinfectants,
which method comprises the step of storing a use of the replaceable cleansing attachment in a cleansing attachment identification device adapted to ensure the replaceable cleansing attachment is used only once,
wherein storing a use in the cleansing attachment identification device comprises storing a first use of the replaceable cleansing attachment on a chip in the replaceable cleansing attachment, and
the method further comprising:
a control board on the base (a) communicating with the chip on the replaceable cleansing attachment, (b) executing software code stored on a memory on the base, and (c) preventing a second use of the replaceable cleansing attachment when the control board determines that the chip has the first use of the replaceable cleansing attachment stored thereon.

8. The method as claimed in claim 7, characterized in that the vibration motor generates a vibration with a frequency of 100 to 5000 Hz.

9. The method as claimed in claim 7, characterized in that the transmission medium is a water-based medium or a gel.

10. The method as claimed in claim 9, characterized in that the water-based medium or gel contains a solvent.

11. The method as claimed in claim 7, which method is carried out using an ultrasound-assisted wound cleanser as claimed in claim 1.

12. A wound-cleansing system comprising:
an ultrasound-assisted wound cleanser in the form of a handheld appliance with a base and a replaceable cleansing attachment attached to the base, an integrated vibration motor, an integrated ultrasound generator, an integrated energy source for the vibration motor and for the ultrasound generator, and wherein the replaceable cleansing attachment can be driven by the vibration motor for the purpose of abrasive removal of fibrin wound coatings, wherein the replaceable cleansing attachment has an acoustic transducer, which is designed to convert the electric oscillations generated by the ultrasound generator into sound waves, a device for transmitting the ultrasound waves, wherein the handheld appliance includes a cleansing attachment identification device adapted to ensure the replaceable cleansing attachment is used only once, wherein the replaceable cleansing attachment has bristles arranged in an inner bristle ring encircling the device for transmitting the ultrasound waves to suppress a propagation of aerosols to the surrounding area and further bristles arranged in an outer bristle ring concentric to the inner bristle ring for the abrasive removal;

wherein the bristles of the inner bristle ring are longer than the bristles of the outer bristle ring, and a transmission medium for transmitting the oscillations into the wound, wherein the cleansing attachment identification device comprises a chip in the replaceable cleansing attachment, and a control board and a memory in the base, wherein after a single use of the replaceable cleansing attachment, the chip is adapted to store a first use of the replaceable cleansing attachment thereon, and wherein the control board is configured to communicate with the chip, execute software code stored on the memory, and prevent a second use of the replaceable cleansing attachment when the chip has the first use of the replaceable cleansing attachment stored thereon.

13. The wound-cleansing system as claimed in claim 12, wherein the transmission medium is a gel or a water-based medium.

14. The wound-cleansing system as claimed in claim 13, wherein the transmission medium contains a solvent or a disinfectant to kill germs.

* * * * *

UNITED STATES PATENT AND TRADEMARK OFFICE
CERTIFICATE OF CORRECTION

| | |
|---|---|
| PATENT NO. | : 11,684,805 B2 |
| APPLICATION NO. | : 15/121952 |
| DATED | : June 27, 2023 |
| INVENTOR(S) | : Jens-Christian Frohwitter |

It is certified that error appears in the above-identified patent and that said Letters Patent is hereby corrected as shown below:

In the Claims

At Column 7, Line 54, "rind" should be -- ring --.

At Column 7, Line 57, "rind" should be -- ring --.

At Column 7, Line 59, "rind" should be -- ring --.

At Column 8, Line 6, "bristles and are" should be -- bristles are --.

Signed and Sealed this
Nineteenth Day of March, 2024

Katherine Kelly Vidal
*Director of the United States Patent and Trademark Office*